US008561474B2

(12) United States Patent
Secq

(10) Patent No.: US 8,561,474 B2
(45) Date of Patent: Oct. 22, 2013

(54) TRIAXIAL CELL FOR THE TESTING OF GEOMATERIALS IN COMPRESSION AND IN TENSION

(75) Inventor: Jean Secq, Villeneuve D'Ascq (FR)

(73) Assignee: Universite des Sciences et Technologies de Lille, Villeneuve d'Ascq (FR)

( * ) Notice: Subject to any disclaimer, the term of this patent is extended or adjusted under 35 U.S.C. 154(b) by 189 days.

(21) Appl. No.: 13/002,725

(22) PCT Filed: Jul. 7, 2009

(86) PCT No.: PCT/FR2009/000836
§ 371 (c)(1),
(2), (4) Date: Jan. 5, 2011

(87) PCT Pub. No.: WO2010/004135
PCT Pub. Date: Jan. 14, 2010

(65) Prior Publication Data
US 2011/0107844 A1      May 12, 2011

(30) Foreign Application Priority Data

Jul. 7, 2008   (FR) ...................................... 08 03851

(51) Int. Cl.
*G01N 3/10*      (2006.01)
*G01N 3/08*      (2006.01)

(52) U.S. Cl.
USPC ............................................. 73/825; 73/826

(58) Field of Classification Search
USPC ................... 73/760, 796, 818, 826, 825, 829
See application file for complete search history.

(56) References Cited

U.S. PATENT DOCUMENTS

| 4,845,995 | A  | * | 7/1989  | Kaste et al. ...................... 73/794 |
| 5,062,303 | A  | * | 11/1991 | Gould et al. ..................... 73/798 |
| 5,095,757 | A  |   | 3/1992  | Larsen et al. |
| 5,959,215 | A  | * | 9/1999  | Ono et al. ........................ 73/798 |
| 6,591,690 | B1 | * | 7/2003  | Crockford ....................... 73/760 |
| 7,040,143 | B2 | * | 5/2006  | Johnson et al. ................. 73/49.3 |
| 7,793,553 | B2 | * | 9/2010  | Lindeman ........................ 73/856 |
| 8,065,929 | B2 | * | 11/2011 | Yakimoski et al. .......... 73/865.6 |

FOREIGN PATENT DOCUMENTS

| EP | 0241715 A    | 10/1987 |
| FR | 2734364 A    | 11/1996 |
| FR | 2746920 A    | 10/1997 |
| JP | 59125039 A   | 7/1984  |
| WO | 2004074762 A | 9/2004  |

* cited by examiner

Primary Examiner — Max Noori
(74) Attorney, Agent, or Firm — Egbert Law Offices, PLLC

(57) ABSTRACT

The invention relates to a triaxial cell for testing geomaterials on specimens. The triaxial cell has at least one piston for subjecting a specimen to stress directed along the longitudinal axis of the specimen. Hydraulic means are provided for subjecting the lateral wall of the specimen to a stress, under the pressure of a fluid. The cell has at least one sealed test chamber-in which the specimen is placed, and a circuit for the controlled pressurization of said test chamber with a fluid, called the pressurizing fluid, and for the controlled draining of said fluid therefrom. The cell has mechanisms for subjecting the specimen to a tensile force, which are configured for removably fastening it between two attachments intended to move apart or closer together under the action of the piston so as to subject said specimen to longitudinal stress or on the contrary to remove the load therefrom.

10 Claims, 2 Drawing Sheets

TRIAXIAL CELL FOR THE TESTING OF GEOMATERIALS IN COMPRESSION AND IN TENSION

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

The invention relates to a triaxial cell for the testing of geomaterials, such as in particular rocks, grounds, is in the form of specimens especially cylindrical in shape.

2. Description of Related Art Including Information Disclosed Under 37 CFR 1.97 and 37 CFR 1.98.

These cylindrically-shaped specimens may be subjected to different pressure, loading, temperature and draining conditions. In order to control these different parameters, the cell may be instrumented with pressure, temperature, internal or external displacement sensors as well as strain gauges. The pressure stresses may be axial, generated under the action of a hydraulic piston and radial on the side face of the specimen under the action of a pressurised fluid.

To that end, documents U.S. Pat. No. 3,975,950 or JP 5,871,432 divulge a triaxial testing cell essay which requires placement in a testing machine acting as a press, generally installed fixedly in laboratories.

To make such a cell autonomous, one may refer to the publication by BROWN S. F. AUSTIN G. AND OVERY, R. F. <<an instrument triaxial cell for cyclic loading of clays>> (GEOTECHNICAL TESTING JOURNAL GJJODJ VOL 3 No 4, December 1980, pages 145 to 152) or still document FR 2,663,123 which divulge a cell with a removable module placed on top of the cell and fitted with its own hydraulic piston capable of generating the axial stress necessary to the test. This autonomous cell thus enables onsite specimen testing, thereby avoiding any transport of specimens for the sampling site of to the to the laboratory.

The aforementioned cells, regardless whether installed fixedly or autonomous present a body comprising a cavity inside which the specimen is placed. The cavity provides between the side wall of the body and that of the specimen a peripheral chamber connected to a pressurising and controlled draining circuit. A fluid may be fed in order to exert a stress on the side surface of the specimen.

In the body, the specimen is positioned between a lower platen of a mount and an upper platen which receives the thrust necessary to the axial stress of a piston. This piston is guided translationally inside a bore through the upper wall of the body which may be monoblock with the side wall of the body or still be in the form of a lid removably fastened, generally screwed to tension rods. In practice, in a cell closed by a lid, when preparing the testing phase, the specimen may be wrapped in a membrane hugging its side wall and being positioned so as to rest on the lower platen. The specimen is covered by the side wall of the body, wherein the lid and its piston then close the cell, especially screwed on. In such a cell, the specimen thus rests simply on the lower platen and is not interconnected with the upper platen. Similarly, the upper platen is not interconnected with the piston of the lid so that it is solely possible to work in compression on the specimen. It should be noted that the same problem is raised for a cell whose upper wall of the body is monoblock with its side wall. However, it may be necessary to stress the specimen axially under tensile force, the difficulty then lies in finding a means for interconnecting the specimen under tensile force when the upper and lower platens, as well as the piston, housed inside the body are no longer accessible. The aim of the present invention is to remedy the drawbacks aforementioned by offering a triaxial cell for the testing of geomaterials enabling to exert onto the specimen a tensile stress especially along the longitudinal axis of the specimen Another aim of the invention is to provide such a cell with easier alignment of the specimen assembly process.

Other aims and advantages will appear in the following description, which is given only by way of example, and without being limited thereto.

BRIEF SUMMARY OF THE INVENTION

Disclosed is a triaxial cell for the testing of geomaterials on specimens, for instance specimens of rock, ground or manufactured materials, comprising at least one piston for subjecting a specimen to a stress directed along the longitudinal axis of the specimen. A hydraulic means is provided for subjecting the lateral wall of the specimen to a stress, under the pressure of a fluid. There is a sealed test chamber inside which the specimen is placed, and a circuit for pressurising and controlled draining of said test chamber with a fluid, called the pressurising fluid.

According to the invention, said cell exhibits means for subjecting the specimen to a tensile force, provided for removably fastening it between two attachments, intended to move apart or closer together under the action of said at least one piston so as to subject said specimen to said longitudinal stress or on the contrary to remove the load therefrom. Said subjecting means include at least, on the one hand two half-shells, situated in said test chamber, respectively interconnected with two elements to be subjected to one another removably, wherein both said half-shells can be contacted when said attachments are brought closer in order to form a sealed shell whereof the internal volume constitutes a depressurising chamber, wherein the outer surface of said sealed shell is subjected, especially possibly, to the action of the pressurising fluid when pressurising said test chamber, or at least the action of the atmospheric pressure and on the other hand, a circuit for putting under vacuum said depressurising chamber.

According to various embodiments both half-shells respectively present two edges with closed periphery intended for co-operating mutually in a leakproof manner, possibly, via a seal. The specimen is cylindrical, the maximum diameter of said shell being greater than the diameter of said specimen. One of the half-shells is subjected to one of the attachments which is formed by said at least one piston, wherein the other half-shell is subjected directly or indirectly by gluing to one of the ends of the specimen. One of the half-shells is subjected to one of the attachments rigidly connected with the stand of the machine, wherein the other corresponding half-shell is subjected directly or indirectly by gluing to one of the ends of the specimen. Said cell includes four half-shells capable of co-operating two by two relative to one another, and wherein on the one hand, one of the half-shells is subjected to one of the attachments which is formed by said at least one piston, the corresponding half-shell being subjected directly or indirectly by gluing to one of the ends of the specimen and, on the other hand, the other half-shell is subjected to the other attachment rigidly connected with the stand of the cell, wherein the other corresponding half-shell is subjected directly or indirectly by gluing to one of the ends of the specimen. The cell exhibits draining means for subjecting the specimen to the longitudinal passage of a draining fluid and comprises at least one circuit for the circulation of a draining fluid. At least one of the half-shells is rigidly connected with a draining mount including a bore for letting through a draining fluid. The specimen is stressed axially between two attachments which are formed respectively by a lower mount and said piston. The cell comprises a body having a cavity forming said test chamber inside which the specimen is accommodated, wherein said body contains between its side wall and that of the specimen a peripheral chamber connected to said pressurising and controlled draining circuit. Said piston is guided in a bore of the upper wall of the body, said wall is integral part of the body or is in the form of an added lid and removably fastened. Said bore of the upper portion of the body includes a section for guiding the piston, a section whereon said bore has a greater diameter, adjusted to slide in a leakproof manner with a flange of the piston by delimiting two annular chambers, respectively lower and upper, wherein a channel for introducing a fluid into the lower annular chamber in order to exert a thrust on said piston, for drawing the specimen. The piston may have a compensation channel which communicates the so-called pressurising fluid of the test chamber and that of said upper annular chamber.

BRIEF DESCRIPTION OF THE SEVERAL VIEWS OF THE DRAWINGS

The invention will be understood better when reading the following description accompanied by the appended drawings among which.

DETAILED DESCRIPTION OF THE INVENTION

Figure 1:
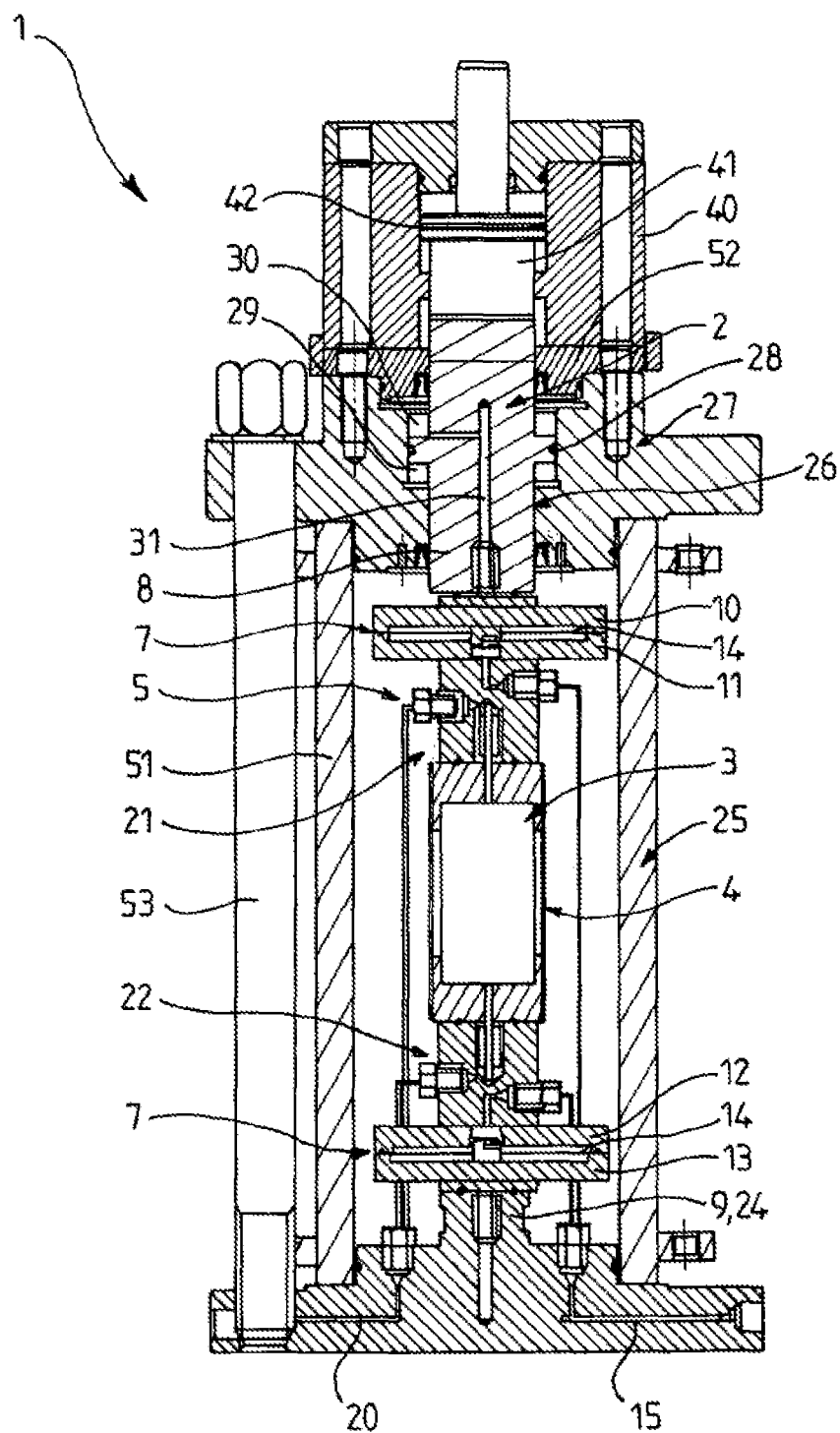
FIG. 1 is a sectional view of a triaxial cell for the testing of geomaterials, especially autonomous and multi-purpose, according to an embodiment of the invention.

Disclosed is a triaxial cell for the testing of geomaterials on specimens, for instance specimens of rock, ground or manufactured materials, comprising at least one piston 2 for subjecting a specimen 3 to a stress directed along the longitudinal axis of the specimen. A hydraulic means is provided for subjecting the lateral wall of the specimen 3 to a stress, especially a radial stress, under the pressure of a fluid, possibly through an elastic envelope 4 enveloping the lateral wall of the specimen 3. Said hydraulic means comprises at least one sealed test chamber 5 inside which the specimen is placed 3, and a circuit for pressurising and controlled draining of said test chamber with a fluid, called the pressurising fluid.

According to the invention, the cell exhibits means 7 for subjecting the specimen to a tensile force, provided for removably fastening it between two attachments 8, 9 intended to move apart or closer together under the action of said at least one piston 2, so as to subject said specimen to said longitudinal stress or on the contrary to remove the load therefrom.

According to the invention, the subjecting means 7 include at least, on the one hand, two half-shells 10, 11; and 12,13 situated in said test chamber 5, respectively interconnected with two elements to be subjected to one another removably, wherein both said half-shells can be contacted when said attachments 8, 9 are brought closer in order to form a sealed shell whereof the internal volume constitutes a depressurising chamber. The subjecting means 7 include at least, on the other hand, a circuit 15 for putting under vacuum said depressurising chamber 14.

Said subjecting process, according to the invention, is hence obtained by the pressure difference between the outside and the inside of the shell, which maintains both half-shells 10, 11; 12, 13 against one another according to an effort greater than the tensile load.

In the case of a simple tensile test, the pressure difference is caused by the atmospheric pressure which is exerted on the external surface of the sealed shell and the pressure inside the shell which is lower than the atmospheric pressure.

In the case of a triaxial essay, the external surface of said sealed shell is subjected to the action of the pressurising fluid when pressurising the test chamber. The pressure difference is caused by the pressure of the pressurising fluid which is exerted on the external surface of the sealed shell and the pressure inside the shell which is lower than the atmospheric pressure.

Figure 2:
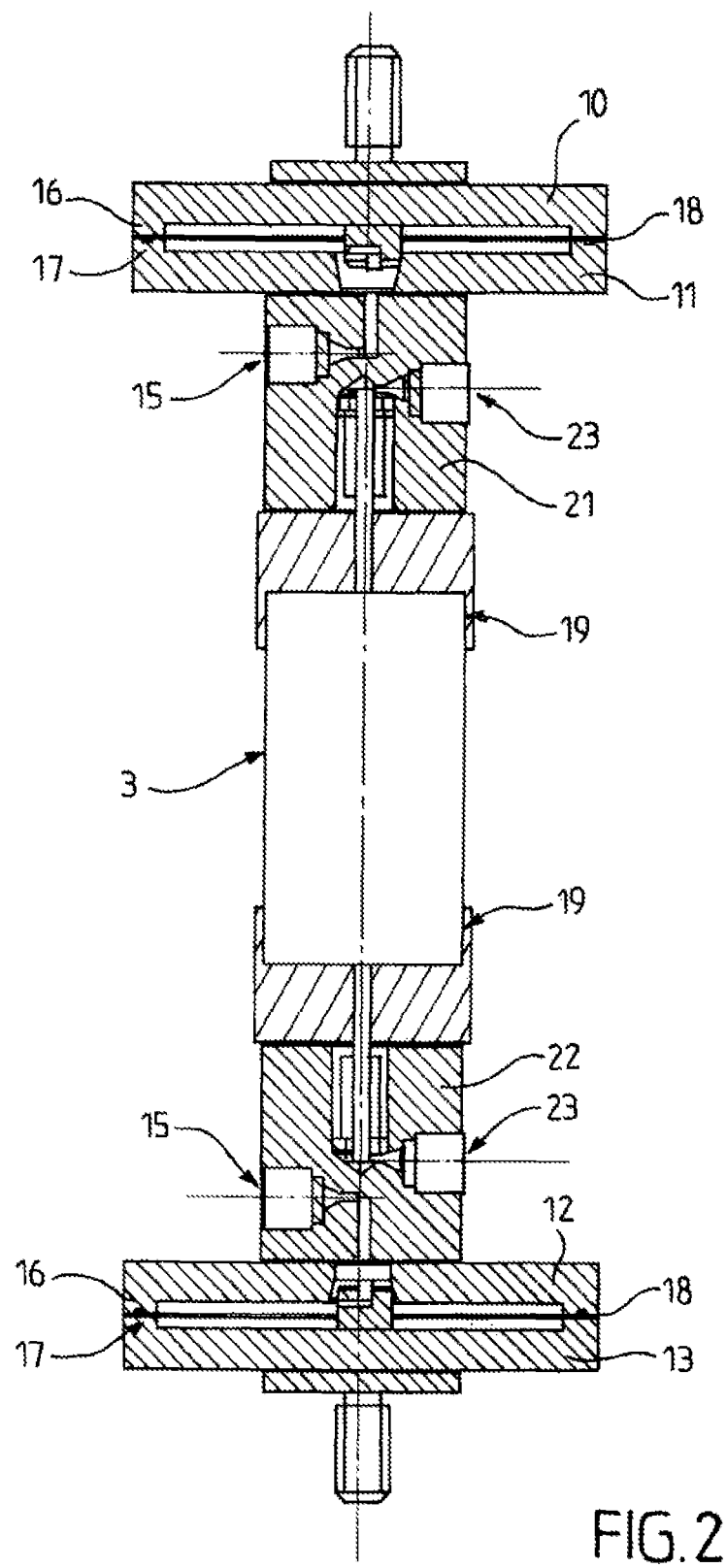
FIG. 2 is a view of the specimen and means for subjecting the specimen to a tensile force illustrated on FIG. 1.

As illustrated on FIG. 2, both half-shells 10, 11 and 12, 13 respectively present two edges 16, 17 with closed periphery intended for cooperating mutually in a leakproof manner, possibly, via a seal 18.

So as to enable significant subjecting process of said shells and thereby high intensity tensile tests, the maximum diameter of said shell is greater than the diameter of the specimen, especially greater than the diameter of the piston 2.

We shall describe therebelow in detail the example illustrated on FIGS. 1 and 2 regarding a so-called multi-purpose triaxial testing cell comprising especially a module on top of said cell to make it autonomous.

However, the invention is not limited to this embodiment and may thus concern a cell which must imperatively be coupled with a laboratory testing machine for operating.

With reference to FIG. 1, the cell comprises a body 25 having a cavity forming said test chamber 5 inside which the specimen 3 is accommodated. The body 25 contains between its side wall and that of the specimen 3 a peripheral chamber connected to a pressurising and controlled draining circuit (non illustrated).

This body 25 is constituted by three dismountable elements, screwed on using tension rods 53, namely a mount 50, a lateral cylindrical wall 51 and a lid 27. The latter comprises a bore 26 for guiding a piston 2 enabling to exert to the specimen the tensile, possibly compression axial stress.

The bore 26 of the upper portion of the body 25, in particular of the lid 27, comprises a section for guiding said piston 2 and a section whereon the bore has a greater diameter, adjusted to slide in a leakproof manner with a flange 28 of said piston, especially via a seal, by delimiting two, respectively lower and upper, annular chambers 29, 30.

A channel (non illustrated) may especially allow the insertion of a fluid into the lower annular chamber 29 in order to exert a thrust on said piston 2 for drawing the specimen 3.

The piston 2 may have, as illustrated, a compensation channel 31 which communicates the pressurising fluid of the test chamber 5 and that of said upper annular chamber 30. The upper radial surface of the flange 28 is then equal to that of the section of the piston 2. Thus, when the piston 2 enters or comes out of the test chamber 5, it does not causes the pressure to increase or to decrease inside the chamber 5 by modifying its volume.

As illustrated on FIG. 1, the piston 2 is inserted into the lid 27 by unscrewing a cap 52 of said lid 27. This cap 52 and the lower portion of the lid 27 are fastened in a leakproof manner thanks to seals for providing for the tightness of the upper annular chamber 30.

The piston 2 protrudes from the lid in order to co-operate with an auxiliary piston 41 of a module 40 secured removably to said lid. This module 40 especially allows making the cell autonomous.

However, it should be noted that this auxiliary piston 40 is of no use for tensile testing since it is not interconnected with the piston 2. It may nonetheless prove useful in the case of cyclic tests where the specimen is successively drawn then compressed.

The module 40 comprises a bore having a section for guiding the auxiliary piston 41 as well as a bore of greater diameter, adjusted to cooperate in a leakproof manner with a flange 42 of said auxiliary piston 41 by delimiting two, respectively lower and upper, annular chambers.

The upper annular chamber will be in particular connected to a channel for introducing a fluid in order to exert a thrust on said piston, for compressing the specimen. It should be noted that the rod of the auxiliary piston 41 may also protrude from the module 40 enabling in particular to couple the cell with a laboratory testing machine or still to measure the external displacement.

We shall describe below the assembly of the specimen for conducting the tensile tests.

With reference to the figures, the cylindrically-shaped specimen 3 is subjected by gluing 19 at its ends respectively, on the one hand, to a lower platen intended for being subjected to the lower mount 24 of said cell and, on the other hand, to an upper platen intended for being subjected to the piston 2 which protrudes downwardly inside the test chamber 5.

The lower and upper platens may be provided with draining means for subjecting the specimen 3 to the longitudinal passage of a draining fluid. The cell comprises to that end at least one circuit marked 20 for circulating the draining fluid.

The lower and upper platens thus constitute draining mounts 21, 22 comprising in particular a bore 23 for letting through the draining fluid. The upper draining mount 21 is integral with a half-shell 11 capable of co-operating removably with a corresponding half-shell 10 attached in particular by screwing to the piston 2.

The lower draining mount 22 is for its own part integral with a half-shell 12 capable of co-operating removably with a corresponding half-shell 13 attached to the lower mount 24, in particular by screwing. When the piston 2 is actuated downwardly towards the specimen, wherein the pairs of half-shells form each a shell whereof the internal volume forms the depressurising chamber 14. The circuit 15 allows putting under vacuum said depressurising chambers, for subjecting the specimen to a tensile force. The cell, according to the invention, advantageously enables to subject the cylindrical specimen 3 to tensile conditions along the longitudinal axis of the specimen. The side wall of the specimen may for its own part undergo a radial stress under the action of the so-called pressurising fluid and thus submit the specimen to different confinement conditions.

It should be noted however that the cell also enables simple tensile tests, unconstrained onto the side wall. The pressure difference between the internal volume of the shells, in the so-called depressurising chamber and that of the testing chamber 5 subjected to atmospheric pressure, then allows to obtain the pressure difference necessary to the subjecting process.

The example above described exhibits four half-shells cooperating two by two for subjecting the specimen to a tensile force, above and below the specimen, respectively with the piston and the mount of the cell.

The subjecting process may be obtained only once the cell has been closed by depressurising both formed shells.

A subjecting solution with two half-shells solely is possible. For example, the piston of the cell and the upper end of the specimen are subjected to a tensile force, using two half-shells, as in the example above described. Conversely, the lower end of the specimen and the mount of the cell may be subjected to a tensile force by any removable attachment means generally known, such as for instance thanks to a bolt system.

In such a case, the lower subjecting process is realised when the cell is open, which allows for screwing for example. The cell is then closed (with the body and the lid). The piston is actuated downwardly until both half-shells form a sealed shell. Finally, the upper subjecting process may be obtained by depressurising the sealed shell.

Naturally, other embodiments could have been contemplated by the man of the art without departing from the framework of the invention defined by the claims below.

I claim:

1. A triaxial cell for the testing of geomaterials on specimens including:
    at least one piston for subjecting a specimen to a stress directed along the longitudinal axis of the specimen;
    hydraulic means for subjecting a lateral wall of the specimen to a stress, under the pressure of a fluid;
    said hydraulic means comprising at least one sealed test chamber inside which the specimen is placed, and a circuit for pressurising and controlled draining of said test chamber with a pressurising fluid, wherein said cell exhibits means for subjecting the specimen to a tensile force, provided for removably fastening it between two attachments intended to move apart or closer together under the action of said at least one piston so as to subject said specimen to said longitudinal stress or to remove the load therefrom; and,
    wherein said subjecting means include at least two half-shells situated in said test chamber, respectively interconnected with two elements to be subjected to one another removably, wherein both said half-shells form a sealed shell when said attachments are brought closer, the internal volume of the sealed shell constituting a depressurising chamber, and a circuit for putting under vacuum said depressurising chamber.

2. A cell according to claim 1, wherein both half-shells respectively present two edges with closed periphery intended for co-operating mutually in a leakproof manner, possibly, via a seal.

3. A cell according to claim 2, wherein the specimen is cylindrical, the maximum diameter of said shell being greater than the diameter of said specimen.

4. A cell according to claim 1, wherein one of the half-shells is subjected to one of the attachments rigidly connected with the stand of the machine wherein the other half-shell is subjected directly or indirectly by gluing to one of the ends of the specimen.

5. A cell according to claim 1, wherein one of the half-shells is subjected to one of the attachments which is formed by said at least one piston, wherein the other half-shell is subjected directly or indirectly by gluing to one of the ends of the specimen.

6. A cell according to claim 1, exhibiting four half-shells capable of co-operating two by two relative to one another, and wherein one of the half-shells is subjected to one of the attachments which is formed by said at least one piston, the corresponding half-shell being subjected directly or indirectly by gluing to one of the ends of the specimen and one of the other half-shells is subjected to the other attachment rigidly connected with the stand of the cell, wherein the corresponding half-shell is subjected directly or indirectly by gluing to the other end of the specimen.

7. A cell according to claim 1, exhibiting draining means for subjecting the specimen to the longitudinal passage of a draining fluid, comprising at least one circuit for the circulation of a draining fluid.

8. A cell insert according to claim 7, wherein one at least of the half-shells is rigidly connected with a draining mount for letting through a draining fluid.

9. A triaxial cell according to claim 1, wherein the specimen is stressed axially between two attachments, which are formed respectively by a lower mount and said piston, which cell comprising a body having a cavity forming said test chamber inside which the specimen is accommodated, wherein said body contains between its side wall and that of the specimen a peripheral chamber connected to said pressurising and controlled draining circuit, said piston being guided inside a bore of the upper wall of the body, which wall is an integral part of the body or is in the form of an added lid and removably fastened, said bore of the upper portion of the body comprising a section for guiding said piston and a section whereon said bore has a greater diameter adjusted to slide in a leakproof manner with a flange of said piston, especially via a seal, by delimiting two, respectively lower and upper, annular chambers, wherein a channel allows the insertion of a fluid into the lower annular chamber in order to exert a thrust on said piston, for drawing the specimen.

10. A cell according to claim 9, wherein the piston has a compensation channel which communicates the so-called the pressurising fluid of the test chamber and that of said upper annular chamber.

\* \* \* \* \*